United States Patent [19]

Xin-shen

[11] Patent Number: 5,098,563
[45] Date of Patent: Mar. 24, 1992

[54] LOW PRESSURE ION CHROMATOGRAPH FOR THE ANALYSIS OF CATIONS

[75] Inventor: Zhang Xin-shen, Chengdu, China

[73] Assignee: Chengdu University of Science and Technology, Chengdu, China

[21] Appl. No.: 647,431

[22] Filed: Jan. 29, 1991

Related U.S. Application Data

[63] Continuation of Ser. No. 362,758, Jun. 7, 1989, abandoned.

[30] Foreign Application Priority Data

Jun. 9, 1988 [CN] China .................. 88105910.2

[51] Int. Cl.$^5$ ............................................ B01D 15/08
[52] U.S. Cl. .................. 210/198.2; 210/961; 324/447; 324/449; 324/450; 422/70; 436/150; 436/161
[58] Field of Search .................. 210/656, 659, 96.1, 210/101, 198.2; 422/70; 436/150, 161; 324/71.1, 425, 324, 438, 439, 446, 447, 448, 449, 450

[56] References Cited

U.S. PATENT DOCUMENTS

| | | | |
|---|---|---|---|
| 2,401,287 | 5/1946 | Yant | 324/447 |
| 3,230,048 | 1/1966 | Skeggs | 422/70 |
| 3,582,475 | 6/1971 | Pretorius | 204/17 |
| 3,648,158 | 3/1972 | Parker | 324/450 |
| 3,665,295 | 5/1972 | Schoen | 324/450 |
| 3,706,381 | 12/1972 | Joynes | 324/449 |
| 3,917,531 | 11/1975 | Magnussen | 210/198.2 |
| 4,032,296 | 6/1977 | Hall | 324/450 |
| 4,265,634 | 5/1981 | Pohl | 422/70 |
| 4,272,246 | 6/1981 | Fritz | 422/70 |
| 4,314,823 | 2/1982 | Rich | 422/70 |
| 4,388,043 | 6/1983 | Preiss | 324/449 |
| 4,446,435 | 5/1984 | Canzoneri | 324/447 |
| 4,554,064 | 11/1985 | McClintock | 422/70 |
| 4,634,982 | 1/1987 | Pungor | 324/447 |
| 4,649,124 | 3/1987 | Hall | 324/449 |
| 4,672,042 | 6/1987 | Ross | 422/70 |
| 4,714,545 | 12/1987 | Bente | 210/101 |
| 4,732,686 | 3/1988 | Small | 422/70 |
| 4,767,279 | 8/1988 | Dourdeville | 210/198.2 |
| 4,767,995 | 8/1988 | Berry | 324/450 |
| 4,840,730 | 6/1989 | Saxena | 210/198.2 |
| 4,861,555 | 8/1989 | Mowery | 422/70 |

FOREIGN PATENT DOCUMENTS

3314578  10/1984  Fed. Rep. of Germany ...... 324/449

OTHER PUBLICATIONS

Gerde, Anion, Chromatography with Low-Conductivity Eluents Journal of Chromatography, 186(1979) pp. 509-519.

Small, Novel Ion Exchange Chromatographic Method Using Conductimetric Detection, Analytical Chemistry, vol. 47, No. 11, Sep. 1975, pp. 1801-1809.

*Primary Examiner*—Ernest G. Therkorn
*Attorney, Agent, or Firm*—Rines and Rines

[57] ABSTRACT

A low pressure ion-chromatograph for the analysis of cations comprises eluent reservoirs, pump, sample injection valve, sampler, column, flow conductivity cell, electrical conductivity detector and recorder, wherein the pump is a low pressure electronic micropump, the angle included between the inlet and outlet of eluent in the cell is 45°-135°, and the flow conductivity cell is oriented in such a position that the eluent inlet is either horizontal or sloping upwardly. There is no leakage in this instrument. No special demands are needed for seal and material. Very good precision and high sensitivity up to ppb level can be obtained, and with low cost.

5 Claims, 4 Drawing Sheets

LOW PRESSURE ION CHROMATOGRAPH FOR THE ANALYSIS OF CATIONS

This application is a continuation of U.S. application Ser. No. 362,758, filed June 7, 1989, now abandoned.

This invention relates to a chromatograph for chromatography analysis, and more particularly to a low pressure ion chromatograph for the analysis of cations.

BACKGROUND OF INVENTION

Ion chromatography is a relatively new type of ion exchange chromatographic technology. H. Small etc. of the Dow Chemical Co., U.S.A., published an article "Novel Ion Exchange Chromatographic Method Using Conductimetric Detection" in Anal. Chem., Vol. 47, 1975, introducing ion chromatography for the first time and embodying an ion chromatograph with a restraint or suppressor column, wherein a low volume and high performance ion exchange agent is used as the packing of the separation column. The detector is a conductivity gauge, and a relatively high pressure Milton-Roy pump is used for transporting the eluent. Disturbance of the eluent conductance at the conductivity detector may be reduced, however, by inserting a restraint/column. D. T. Gjerde and J. S. Fritz et al. published their article "Anion Chromatography with Low-Conductivity Eluent" in J. Chromatography Vol. 186, 1979. They also produced an ion chromatograph without a restraint column but still required a relatively high pressure Milton-Roy pump (200–450 p.s.i.—or 14–31 $kg/cm^2$) to transport the eluent, and employed a conductivity gauge as the detector.

At present, such prior ion chromatographs for the analysis of cations, however, have the following disadvantages:

(1) High pressure requirement (said 14–31 $kg/cm^2$) for joints, pipes and valves.
(2) Leakage often takes place.
(3) Complicated structure.
(4) High cost—about $40,000–$100,000 per set.

OBJECT OF INVENTION

The object of this invention, accordingly, is to provide a novel ion chromatograph that overcomes the above-identified current technical problems, providing a high precision and low cost and relatively low pressure ion chromatograph for cation analysis.

SUMMARY

In summary, the invention embraces in a low pressure ion-chromatograph as for the analysis of cations and in which eluent is pumped through a sample injection valve through a sampler and into a chromatographic separation column, the combinations of a flow conductivity cell having en eluent inlet and outlet disposed in a cell block at an angle $\beta$ with respect to one another, a low pressure electronic micropump connected to pump the said eluent from the said separation column to the said cell eluent inlet and out the said outlet; the said cell eluent inlet serving as one cell electrode and being axially disposed in the said cell block in-line with a second electrode spaced a predetermined distance along such line from the inlet-electrode to define a gap therebetween, with the said outlet extending at said angle $\beta$ from said gap; and electronic conductivity detector and recording means connected to said outlet. Preferred and best mode designs and details are later presented.

BRIEF DESCRIPTION OF THE DRAWINGS

FIG. 2(I) showing a flow conductivity cell with constant distance between its two electrodes and FIG. (II) showing adjustable electrode separation distance.

DESCRIPTION OF THE PREFERRED EMBODIMENT

Figure 1:
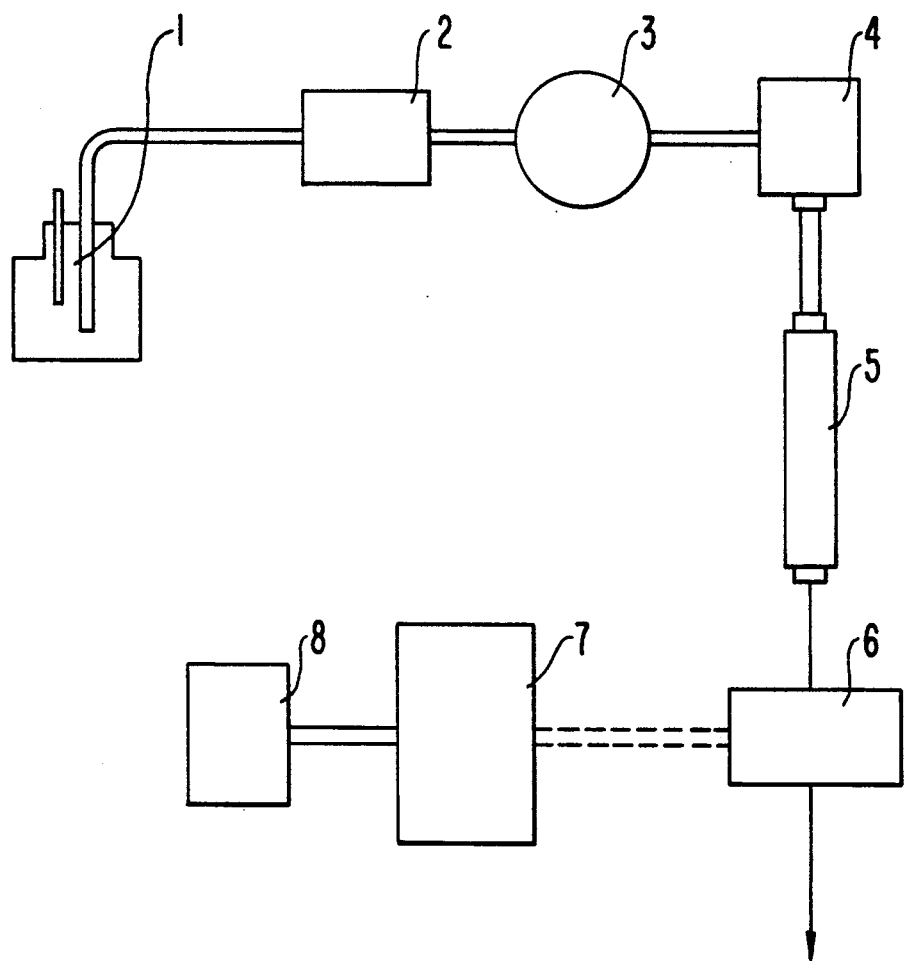
FIG. 1 is a block diagram of the invention in preferred or best mode form.

Referring to the preferred embodiment of low pressure ion chromatograph of FIG. 1, the system is shown in FIG. 1 comprising eluent reservoirs (1), low pressure pump (2), sample injection valve (3), sampler (4), chromatographic separation column (5), flow conductivity cell (6), conductivity detector (7) and recorder (8).

Figure 2I:
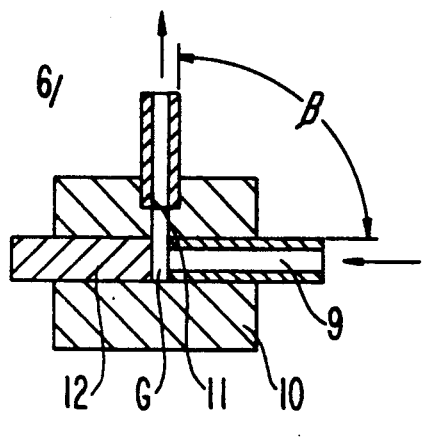
FIGS. 2(I) and (II) are transverse sections of novel flow conductivity cells for use in the system of FIG. 1.

As before stated, in accordance with the novel cell design of the invention, the pump (2) is a relatively low pressure electronic micropump and the cell itself is designed with the angle $\beta$ included between eluent inlet (9) and outlet (11) of flow conductivity cell (6) in the range of 45°–135°, FIGS. 2(I) and (II).

Figure 2:
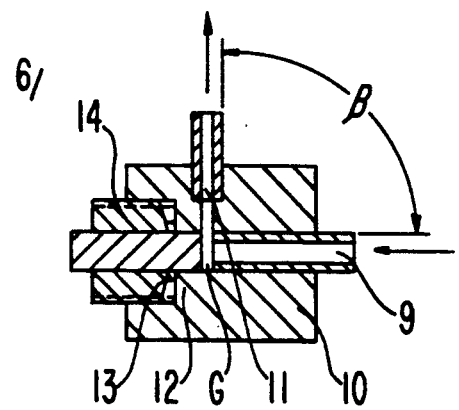

Turning to the two types of the flow conductivity cell (6) useful in this invention, FIG. 2, one is a flow conductivity cell with a constant distance or gap G between the two cell electrodes, as shown in FIG. 2(I), and the other type provides for adjustable distance between the two electrodes, as shown in FIG. 2(II). The flow conductivity cell with constant distance or gap G is composed of eluent inlet (9), FIG. 2(I), also serving as an electrode, cell block (10), eluent outlet (11), and a second electrode (12), shown as a solid conductor. The hollow eluent inlet-electrode (9) and electrode (12) are inserted horizontally into opposite sides of the cell block (10) and are fixed in the cell block (10) with their axes aligned. The gap G wherein analysis occurs between the electrodes is shown below the eluent outlet 11, aligned thereabove—at $\beta=90°$ in the drawings.

The flow conductivity cell of adjustable electrode distance G, FIG. 2(II), is composed of fixed eluent-electrode inlet (9), cell block (10), eluent outlet (11), and an adjustable electrode (12), held with gasket (13) in an adjustable electrode sleeve (14). The eluent inlet-fixed electrode (9) is inserted into one side of the cell block (10) and horizontally fixed to the cell block (10). The adjustable electrode (12) is inserted into the opposing side of the cell block (10) and horizontally fixed to the cell block (10) by means of the gasket (13) and the adjustable electrode sleeve (14) with the axes of the two electrodes again aligned. The distance or gap G between the two electrodes may be adjusted by sliding the adjustable electrode sleeve (14) or by changing the gasket thickness.

Figure 3I:
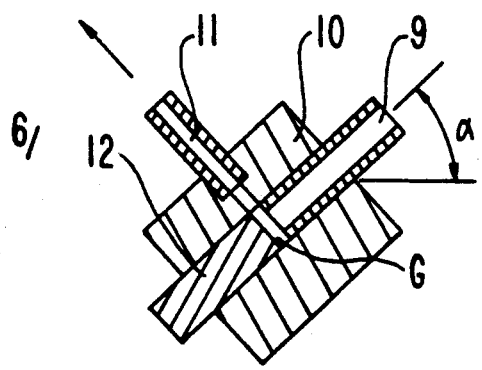
FIGS. 3(I) and (II) are similar to FIG. 2(I) and (II), respectively, with angularly oriented flow conductivity cell positions.

The flow conductivity cell itself is positioned, FIGS. 3(I) and (II), by rotating the cell block (10) so that the angle $\alpha$ included between eluent inlet (9) and the horizontal may vary from 0°–60°; that is, the position of eluent inlet is in horizontal or upwardly sloping position. The optimum position of the flow conductivity cell is with the angle $\alpha$ between eluent inlet (9) and the horizontal of 45°.

In the structure of the flow conductivity cell shown in FIGS. 2(I) and 3(I), the distance G between the two electrodes is constant and the angle $\beta$ included between eluent inlet (9) and the outlet (11) is 90°. The eluent inlet-electrode, the eluent outlet, and the electrode (12) are preferably made of stainless steel. The cell body may be made of plexiglass (polymethyl methacrylate). The flow conductivity cell is shown in FIGS. 3(I) and (II) positioned with an angle $\alpha$ included between the eluent inlet of the cell and the horizontal line of 45°.

An example of useful relatively low pressure pumps 2, FIG. 1, of the previously described several or few kg/cm² low pressure range now made possible by this cell design, are the 1988 Models LDB-M and LDB-H electronic peristaltic pumps (also called electronic micropumps) made by the Dingshan Instrument Factory in Xiangshal County, Zhejiang province, PRC, having the following main specifications:

| 1. flow: | |
| --- | --- |
| ($\phi \times \phi_3$ Single pipe) | 0.05–100 ml/h continuously adjustable |
| ($\phi_4 \times \phi_6$ Single pipe) | 1–1000 ml/h continuously adjustable |
| 2. maximum output pressure | 0–5 kg/cm² continuously adjustable |
| 3. continuous working time | 200 hours |
| 4. power | 15 w |
| 5. work environment | 0°–40° C. <80% relative humidity |
| 6. weight | 2 kg (model M) 2.7 kg (model H) |

The 1988 Model WLB-78A electronic micropump of Guokang Instrument Factory in Xinchang country, Zhejiang province, PRC, may also be used. The main specifications are the same as Model LDB-M, LDB-H, but the maximum output pressure is within the relatively low pressure range of 0–3.5 kg/cm².

EXAMPLE 1

Figure 3:
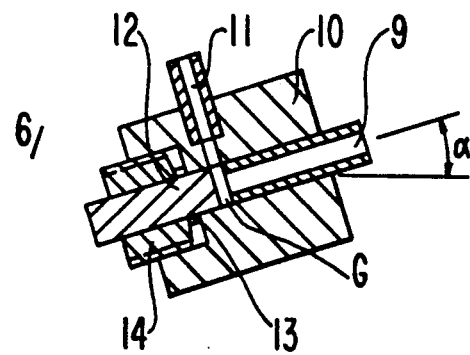
Figure 4:
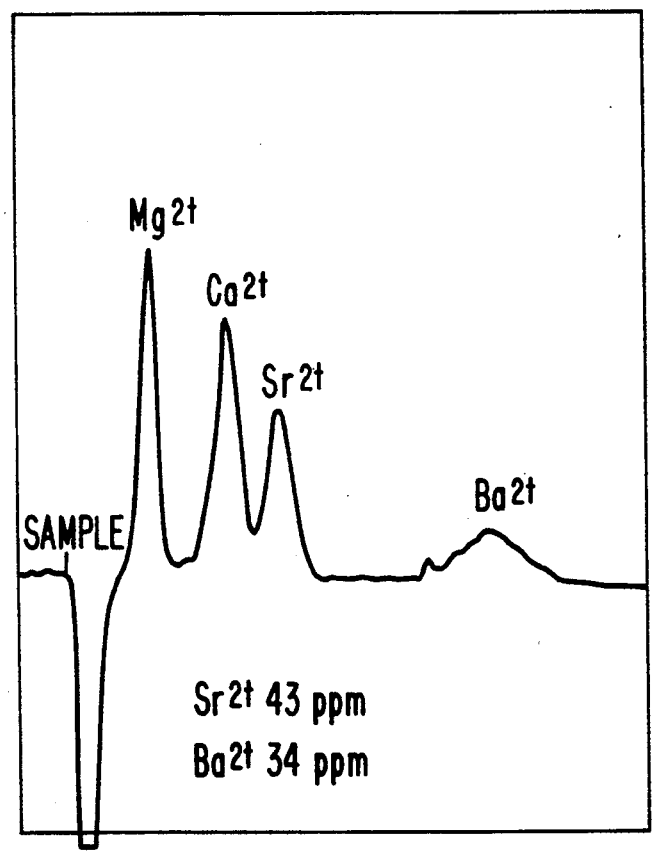
FIGS. 4 and 5 are respectively alkaline earth and alkaline metal ion chromatographs obtained with the apparatus of the invention.

FIG. 4 is a chromatogram of alkaline-earth metal ions $Mg^{2+}$, $Ca^{2+}$, $Sr^{2+}$, $Ba^{2+}$, which were analysed simultaneously with the system of FIGS. 1–3. The chromatographic conditions were the following:

The chromatographic separation column was packed with the earlier mentioned ion exchange material of said articles, as reconstructed by the inventor. The characteristics of the packing are steady structure, good reproducibility and fine permeability, Eluent: $10^{-3}M$ ethylenediamine. Electric conductivity detector: set at 2 mv. Paper speed: 4 mm/min. Working low pressure: 2 kg/cm². Flow: 1.2 ml/min. Sample: 200 $\mu$l.

EXAMPLE 2

Figure 5:
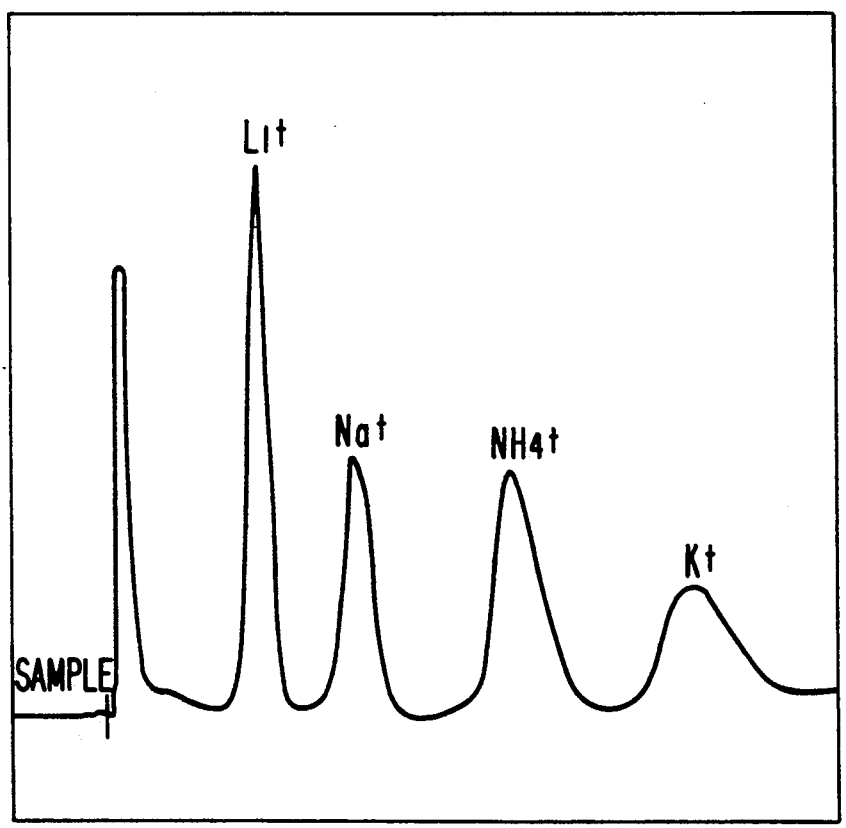

FIG. 5 is a chromatogram of alkaline metal $Li^+$ $Na^+NH_4^+K^+$ etc. ions which were simultaneously analysed by the invention. The chromatographic conditions are the same as the chromatographic conditions for the alkaline-earth metals of Example 1, except that eluent was $7.2 \times 10^{-4}M$ nitric acid.

Compared with prior art, the invention has the following advantages:

1. A low pressure electronic micropump (of order of 2–3.5 kg/cm²) is used instead of relatively high pressure pumps, as of the before-mentioned Milton-Roy pump types (of order of 14–31 kg/cm²), minimizing or eliminating leakage problems and lowering the requirement for seals and pressure-resisting materials.

2. Good baseline stability, low baseline noise and little drift are attained due to the improved flow conductivity cell.

3. High analysis precision and sensitivity is attained, reaching the ppb level.

4. Lower cost is attained. In the P.R.C., only about 1800 RM B/set—about $300 U.S. (not including recorder).

5. A simple structure is provided with convenient operation and easy maintenance.

6. There is no need for the use of restraint columns and reproductive devices.

The invention, moreover, not only can be used for cation analysis for environmental monitoring and for medical, pharmaceutical, geological, food, agricultural and forestry applications, as illustrations, but it also can be used as a general conductivity gauge to determine conductivity of ordinary solutions and to carry out conductometric titration. It also can be used as a gel filter chromatograph (GFC) if the column is changed to, for example, a Cephadex G25, G10 etc. chromatographic separation column.

Further modifications will occur to those skilled in this art and such are considered to fall within the spirit and scope of the invention as defined in the appended claims.

What is claimed is:

1. In a low pressure ion-chromatograph for the analysis of cations and in which eluent is pumped through a sample injection valve through a sampler and into a chromatograph separation column, the combination of a flow conductivity cell having an eluent inlet and outlet disposed in a cell block at an angle $\beta$ with respect to one another in which said angle $\beta$ is within the range of substantially 45° to 135°, a low pressure electronic micropump connected to pump the said eluent from the said separation column to the said cell eluent inlet and out the said outlet, and with said low pressure and the resulting operating pressure in the ion-chromatograph being adjusted to a pressure of the order of 2–3.5 kg/cm²; the said cell eluent inlet serving as one cell electrode and being axially disposed in the said cell block in-line with a second electrode spaced a predetermined distance along such line from the inlet-electrode to define a gap therebetween, with the said outlet extending at said angle $\beta$ from said gap; and electronic conductivity detector and recording means connected to said outlet.

2. An ion-chromatograph as claimed in claim 1 and in which $\beta = 90°$.

3. An ion-chromatograph as claimed in claim 1 and in which means is provided for adjusting the distance of said gap along said line.

4. An ion-chromatograph as claimed in claim 1 and in which the cell is oriented at an angle $\alpha$ from the horizontal within the range of 0° to 60°.

5. An ion-chromatograph as claimed in claim 4 and in which $\alpha$ is adjusted to substantially 45°.

* * * * *